(12) United States Patent
MacDonald et al.

(10) Patent No.: US 9,186,460 B2
(45) Date of Patent: Nov. 17, 2015

(54) ASSEMBLY OF A DRUG DELIVERY DEVICE

(75) Inventors: Catherine Anne MacDonald, Ashby-de-la-Zouch (GB); Robert Veasey, Leamington Spa (GB); Garen Kouyoumjian, Leamington Spa (GB); Christopher Jones, Tewkesbury (GB); Andrew Mark Lindsay, Hinckley (GB); Michael Bainton, Kineton (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 154 days.

(21) Appl. No.: 13/498,440

(22) PCT Filed: Sep. 29, 2010

(86) PCT No.: PCT/EP2010/064432
§ 371 (c)(1),
(2), (4) Date: Aug. 3, 2012

(87) PCT Pub. No.: WO2011/039239
PCT Pub. Date: Apr. 7, 2011

(65) Prior Publication Data
US 2012/0296285 A1    Nov. 22, 2012

(30) Foreign Application Priority Data

Sep. 30, 2009  (EP) .................................... 09171771

(51) Int. Cl.
*A61M 5/315*      (2006.01)
*A61M 5/24*       (2006.01)
*A61M 5/31*       (2006.01)

(52) U.S. Cl.
CPC .............. *A61M 5/24* (2013.01); *A61M 5/3146* (2013.01); *A61M 5/3155* (2013.01);
(Continued)

(58) Field of Classification Search
CPC ............ A61M 5/3155; A61M 5/3151; A61M 5/3148; A61M 5/31563; A61M 5/31585; A61M 5/24; A61M 5/3158
USPC .................................. 604/187, 207, 208, 211
See application file for complete search history.

(56) References Cited

U.S. PATENT DOCUMENTS

| 5,514,097 A * | 5/1996 | Knauer .......................... 604/136 |
| 2004/0019333 A1* | 1/2004 | Graf et al. ...................... 604/207 |
| 2011/0251553 A1* | 10/2011 | Ratjen et al. ..................... 604/89 |

FOREIGN PATENT DOCUMENTS

| WO | 0062847 A1 | 10/2000 |
| WO | 2004007000 A1 | 1/2004 |
| WO | 2008058665 A1 | 5/2008 |

OTHER PUBLICATIONS

Form PCT/IPEA/416, Notification of Transmittal of the International Preliminary Report on Patentability.
(Continued)

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

An assembly of a drug delivery device comprises a body (10) having a distal end (11) and a proximal end (12), a drive assembly (4) arranged substantially within the body (10) to facilitate dispense of a medicinal product and a button member (5) arranged at the proximal end (12) of the body (10) and adapted to act upon the drive assembly (4). The drive assembly (4) has an initial pre-ready state, a transient state and a ready state; in the pre-ready and transient states the button member (5) is twistable with respect to the body (10) to act upon the drive assembly (4) and wherein in the ready state the button member (5) is axially moveable but not substantially twistable with respect to the body (10) to act upon the drive assembly (4) to dispense a dose of the medicinal product.

17 Claims, 13 Drawing Sheets

Figure 1:
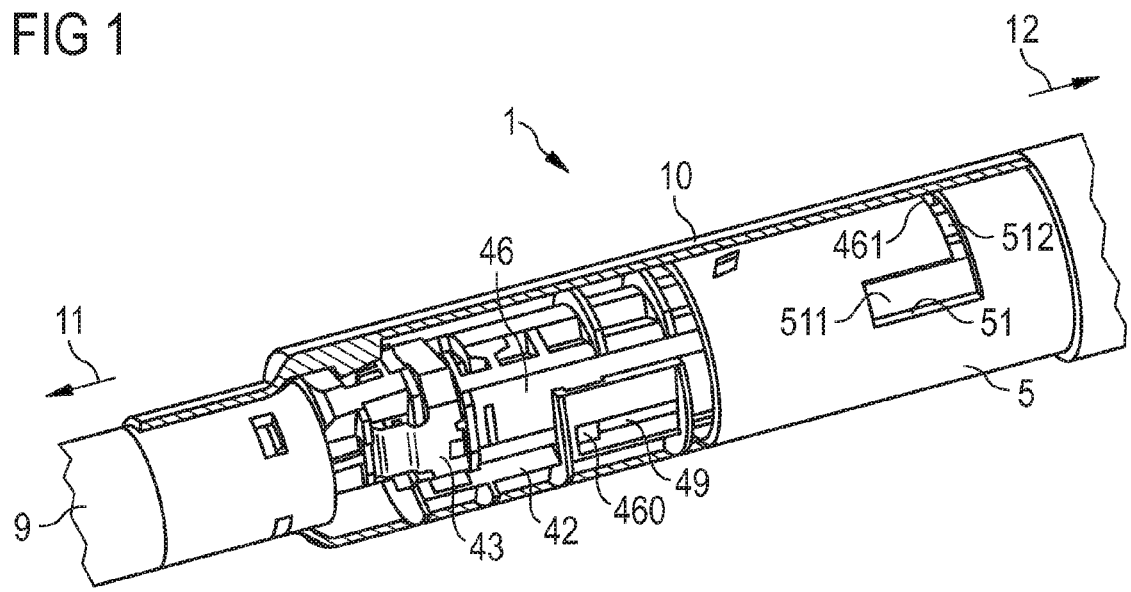

(52) U.S. Cl.
CPC ........ *A61M 5/3158* (2013.01); *A61M 5/31593* (2013.01); *A61M 5/2448* (2013.01); *A61M 5/3156* (2013.01); *A61M 5/31551* (2013.01); *A61M 5/31555* (2013.01); *A61M 2005/2407* (2013.01); *A61M 2005/2492* (2013.01); *A61M 2205/583* (2013.01); *A61M 2205/6018* (2013.01)

(56) References Cited

OTHER PUBLICATIONS

English Translation of Japanese Patent Application No. 2012-531402 Notice of Reasons for Refusal dated Jul. 15, 2014.

* cited by examiner

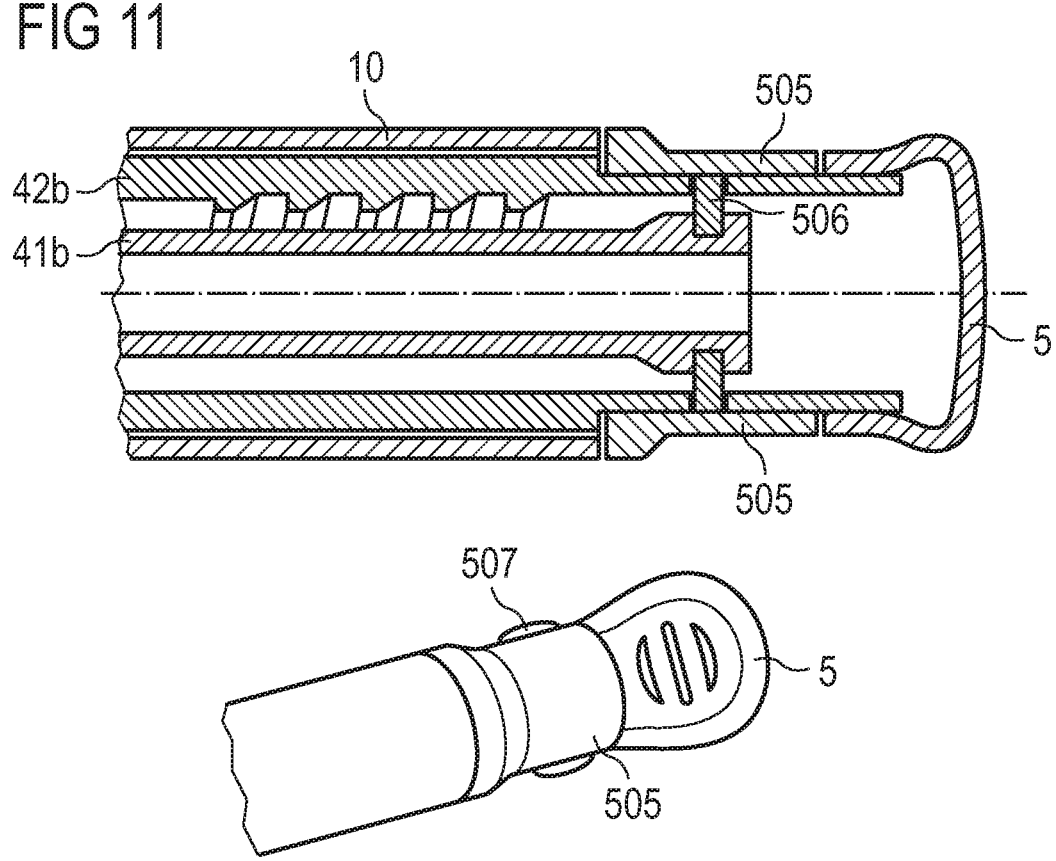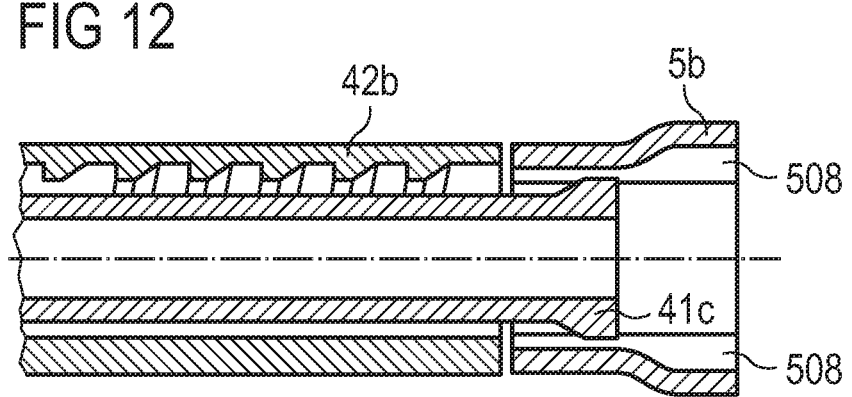

FIG 15
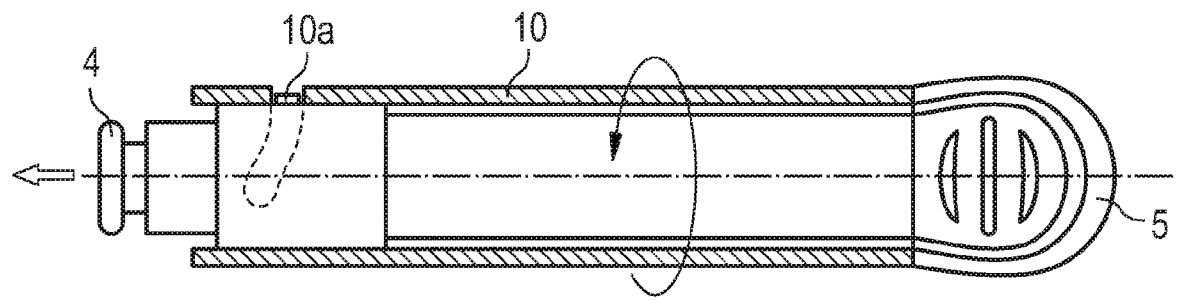
FIG 16A
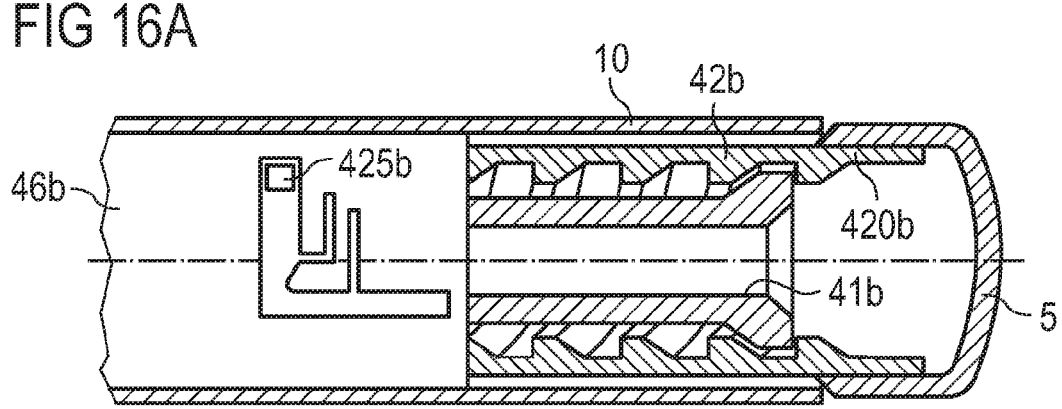
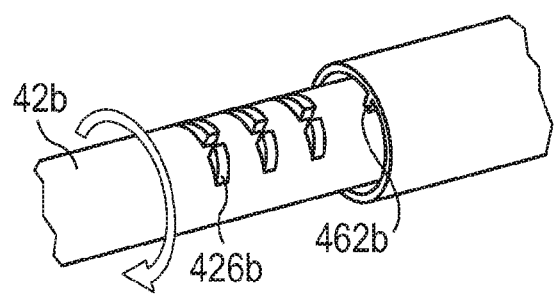

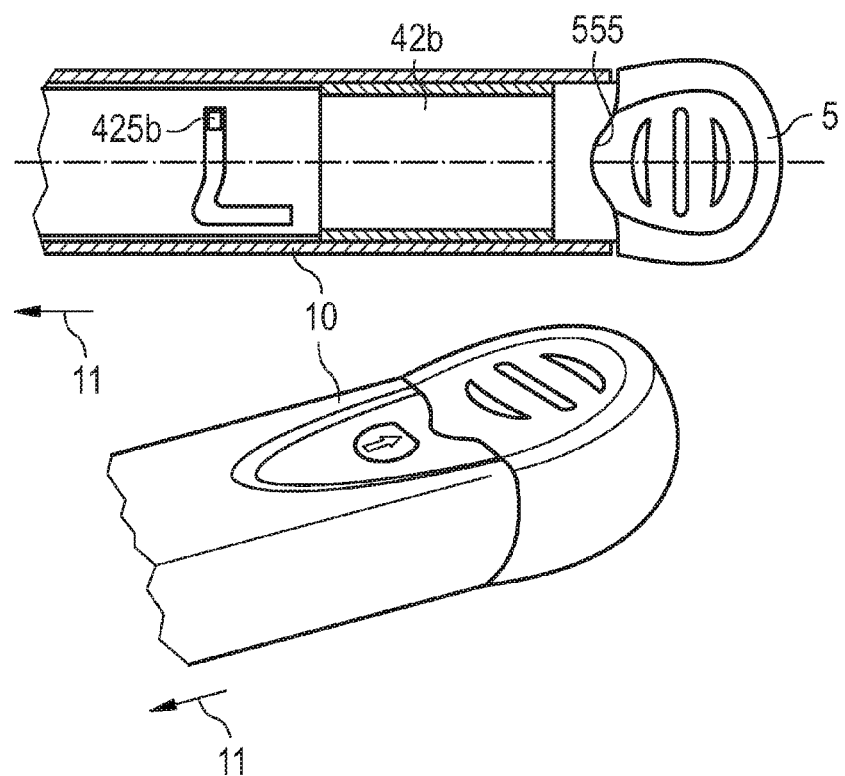
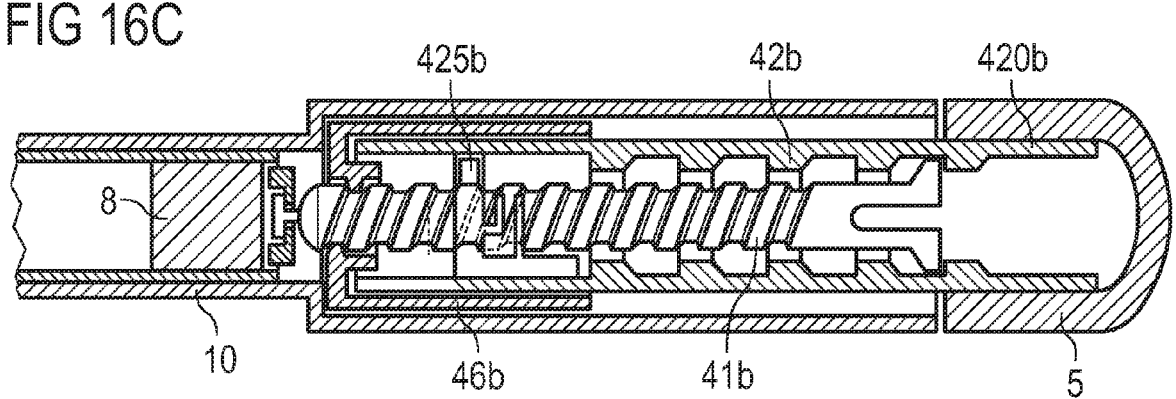

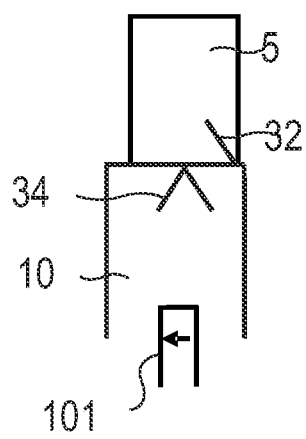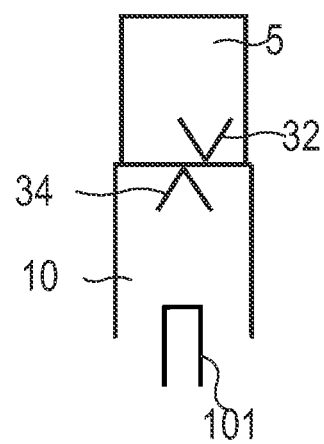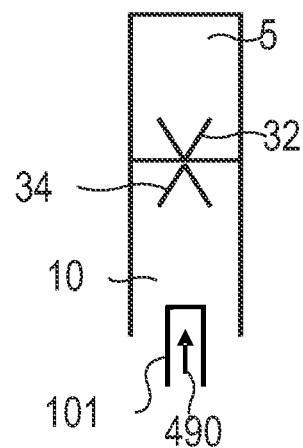

ASSEMBLY OF A DRUG DELIVERY DEVICE

CROSS REFERENCE TO RELATED APPLICATIONS

The present application is a 35 U.S.C. 371 National Application of PCT/EP2010/064432 filed Sep. 29, 2010, which claims priority to European Patent Application No. 09171771.0, filed Sep. 30, 2009, the entire contents of which are incorporated entirely herein by reference.

The present invention relates to an assembly of a drug delivery device. The invention is also related to a drug delivery device, in particular to a pen-type injector. Also, the invention relates to a button member, in particular a button member for operating a drive assembly of a drug delivery device.

DESCRIPTION OF RELATED ART

Drug delivery devices are generally known for administration of a medicinal product into a patient's body. Depending on the drug delivery device, some of them are suitable for self-administration by a patient. Such medicinal product may include, for instance, insulin, growth hormones, heparin, but are not restricted thereto. The medicinal product may be administered on an irregular basis over a short-term or a long-term period. It may also be often necessary that the amount of dose administered into a patient's body is very accurate and does also not differ between different doses.

Before administering the first dose of the medicinal product, the assembly of such a device, must be prepared to take up the tolerances that are inherent in manufacture of the device to ensure an accurate first dose. A patient, who is unfamiliar with such preparation, may fail or incorrectly prepare the device before dispensing and administering the first dose. Further, as the drug delivery device may be used on an irregular basis, a patient may forget or become confused about the fact whether the drug delivery device has already been prepared or not.

Therefore, there is a need for improving the assembly of drug delivery devices and for such devices to clearly indicate their preparation state to a user.

Independent claim 1 meets this requirement. Aspects and several embodiments are subject to the dependent claims.

The term "assembly of a drug delivery device" corresponds to the term drug delivery device.

The term "medicinal product" or the term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

An assembly of a drug delivery device according to the proposed principle comprises a first operating state, called pre-ready state, and at least a second state, called ready state. It may also comprise a transient state, which chronologically follows the pre-ready state and is chronologically ahead the ready state. The ready state may directly follow the transient state.

In this respect, the pre-ready state implies a state of the assembly of the drug delivery device, in which the drug delivery device is unprepared for facilitating dispense of doses of a medicinal product. In other words, the drug delivery device has still to be prepared for dispensing a medicinal product. During preparing the assembly of the drug delivery device for facilitating dispense of the medicinal product and particularly facilitating the deliberate and desired dispense of a medicinal product, the assembly of the drug delivery device is in the transient state.

The term facilitating dispense of a medicinal product implies any procedure upon the drug delivery device, resulting in a delivery of the medicinal product, including, but not limited thereto, setting up a dose of a medicinal product and dispensing the dose.

The transient state implies the state of the drug delivery device, in which the device is being prepared for facilitating dispenses of a medicinal product. The user may conduct some specific action upon the drug delivery device to prepare the device for a later dispense of the medicinal product.

As soon as the assembly of the drug delivery device has been fully prepared and the transient state completed, the user is able to correctly dispense a dose of a medicinal product, the assembly of the drug delivery device is considered to be in the ready state. In the ready state, the user may act upon the drug delivery device to set up and deliberately dispense the desired amount of medicinal product. For this purpose, the user may conduct some specific action on the drug delivery device. Said action conducted by the user may be different from the action conducted by the user during the pre-ready state and the transient state. Accordingly, the ready state is subsequent to the transient and the pre-ready state.

In other words, the assembly of the drug delivery device in its pre-ready and the transient state is not able to deliberately dispense a specific and desired amount of medicinal product. In the pre-ready state, the user may act upon the drug delivery device to prepare the drug delivery device for dispensing a dose of medicinal product, which puts the drug delivery device into its transient state.

The assembly of the drug delivery device may allow only a specific operation in the pre-ready state and during the transient state, which is completely different from the operation allowed by the user in the ready state of the assembly of the drug delivery device. Such actions conducted by the user to prepare the device for dispensing a medicinal product and setting up and dispensing a medicinal product are different. So, a user can distinguish between the different states due to the different actions allowed.

In an embodiment, the assembly of the drug delivery device may comprise a body having a distal end and a proximal end. The term body may imply the external structure like for example a main body portion or an outer shell of the drug delivery device. The term body may correspond to the term housing, but may also comprise a housing, which might comprise a cartridge holder.

The body may be manufactured from plastics and may include some markings for the user indicating the amount of medicinal product to be delivered, the medicinal product itself or any other kind of usage information of the drug delivery device. The body may comprise different outer shapes with respect to the proximal and distal end indicating together with other parts of the drug delivery device the current state, which the drug delivery device takes up.

A drive assembly may be arranged at least partly within the body to facilitate dispense of a medicinal product. The term drive assembly may imply a structure within the body which a user may act upon during operation of the drug delivery device. The drive assembly may comprise one or more different portions, which may be partly arranged within the body and partly outside the body.

During operation of the device, different mechanical parts of the drive assembly may act upon each other to facilitate dispense of the medicinal product. In this respect, the drive assembly may be adapted to set up a dose of medicinal product to be delivered and to dispense this set dose in a subsequent step.

The drive assembly may comprise an element, said element arranged at least partly within the body and axially displaceable towards the distal end of the body. Such element may be, but is not restricted thereto, a piston rod or a lead screw. The piston rod may comprise some teeth-like elements acting upon other parts of the drive assembly, thereby allowing displacement of the piston rod towards the distal end. The piston rod may also comprise a sleeve which performs a twist movement in order to be displaced towards the distal end. Accordingly, the drive assembly may comprise an element which is rotated or screwed to axially move towards the distal end.

The assembly of the drug delivery device may also comprise a button member. The term button member may apply to a member which can be located at the proximal end of the drug delivery device. The user may act upon the button member to operate the drug delivery device. The operation of the button member by the user may include, but is not limited thereto, a rotation of the button member, a twist of the button member, a movement of the button member parallel to a longitudinal axis of the drug delivery device, push- or pull operation of the button. Accordingly, the button member may be movable relative to the body of the drug delivery device. The button member may also be either rotatable or axially movable relative to the body.

In an embodiment, the button member is arranged at the proximal end of the body and adapted to act upon the drive assembly. In this respect, the button member may act upon the drive assembly to facilitate dispense of a medicinal product. Such acting upon the drive assembly may include, but is not limited thereto, moving some parts of the drive assembly, rotating some parts of the drive assembly, pulling or pushing some parts of the drive assembly and axially displacing some parts of the drive assembly. Moving, rotating and/or displacing those parts will act in turn upon other parts of the drive assembly, thereby in summary resulting in the desired action of the drive assembly.

The drive assembly itself may comprise an initial pre-ready state, a transient state and a ready state. The term pre-ready state with respect to the drive assembly implies the state in which the drive assembly is not capable of facilitating dispense of a desired amount of a medicinal product. Accordingly, the initial pre-ready state is the state in which the drive assembly is before the first use. The pre-ready state of the drive assembly may correspond to the pre-ready state of the drug delivery device.

During the transient state, the drive assembly is being prepared for later operation and particularly to facilitate dispense of the desired dose of medicinal product.

The terms preparation, preparing operation or preparing implies any operation upon the drive assembly to prepare the drive assembly for later facilitating dispense of the medicinal product. Such operation may include moving and/or displacing parts of the drive assembly to compensate any backlashes or tolerances between different mechanical parts. It may also include moving parts of the drive assembly, for instance the piston rod or the lead screw at least partly towards the distal end of the drug delivery device.

In an embodiment, an assembly of a drug delivery device comprises a body having a distal end and a proximal end. A drive assembly may be arranged substantially within the body to facilitate dispense of a medicinal product. A button member is arranged at the proximal end of the body and adapted to act upon the drive assembly. This may include moving parts of the drive assembly upon movement of the button member. The drive assembly has an initial pre-ready state and a ready state, wherein in the pre-ready state, the button member is twistable with respect to the body to act upon the drive assembly. In the ready state, the button member is axially movable but not substantially twistable with respect to the body to act upon the drive assembly to dispense a dose of the medicinal product.

In the embodiment, the button member can be twisted with respect to the body during the pre-ready state, thereby initiating the transient state of the drive assembly. The term transient state implies the state in which a user acts upon the button member to prepare the drug delivery device for facilitating correct dispense of a medicinal product. During the transient state, the button member may act upon the drive assembly to prepare the drive assembly and parts of the drive assembly for later use in the ready state of the drug delivery device. The pre-ready state and transient state of the drive assembly may correspond to the respective states of the drug delivery device.

The term twist movement or twistable button member implies any movement of the button member which comprises a rotational component with respect to the body. Accordingly, the button member can be purely rotated or moved along a helical path comprising a pure rotational component and an axial movement component. A twist movement of the button member may imply a movement having two subsequent steps, of which at least one comprises a rotational component. For instance, the button can be rotated in a first step and then partly axially moved in a second step. It can also be axially moved first and then rotated in a subsequent second step. The term twist also implies any combination of rotation and axial movement.

At the end of the transient state, the button member may be prevented from being twisted with respect to the body in the reverse direction. In other words, the button member is prevented from being rotated or moved backwards, at least at the end of the transient state. Accordingly, at the end of the transient state, the drive assembly and the drug delivery device is fully prepared for correctly dispensing the desired amount of the medicinal product.

The term ready state of the drive assembly implies a state in which the drive assembly is fully prepared for dispensing a desired amount of the medicinal product. In the ready state, the button member can be axially moved but not substantially rotated and/or twisted with respect to the body to act upon the drive assembly. Consequently, the possible movements of the button member in the pre-ready state and during the transient state may be completely different from any possible movement of the button member during the ready state of the drive assembly.

The different possible movements of the button member during the pre-ready and transient state and the ready state of the drive assembly and the drug delivery device, respectively, indicate different operating states to the user. This allows the user to identify the current state in which the assembly of the drug delivery device and the drive assembly take place.

The drug delivery device may comprise a fluid reservoir. The term fluid reservoir implies any reservoir which is capable of holding a fluid, a powder or any other substance. The fluid reservoir may comprise an aperture through which the substance can be dispensed.

A bung may act upon the fluid reservoir to dispense the substance, for instance the medicinal product. The fluid reservoir and bung may be included in a cartridge or a detachable cartridge. The cartridge may comprise a cartridge holder, in which the fluid reservoir is arranged. A bung can be arranged within the cartridge holder at its proximal end. The cartridge and cartridge holder may be part of the drug delivery device, but may also be reversibly detachable from the body. The piston rod may be arranged to drive the bung, in particular distally with respect to the cartridge.

During the transient state, the button member may act upon the drive assembly to prepare the drug delivery device. The term prepare the drug delivery device may imply any operation of the drug delivery device or parts thereof to prepare the device for facilitating dispense of a medicinal product. The term prepare may include, but is not restricted to priming the device, to mixing a medicinal product, to expelling a fluid or air.

The term prime implies a process of the drive assembly in which tolerances or backlashes between different mechanical parts of the drive assembly are compensated. This may include displacing parts of the drive assembly, like for instance the piston rod or the lead screw towards its distal end. Further, the term prime may imply a process in which the gap between a part of the drive assembly like, for instance, the piston rod or the lead screw and a part of a cartridge assembly, like for instance a bung, is closed. The term prime may also imply a state in which a small amount of fluid or a medicinal product is expelled from the assembly of the drug delivery device.

The term mix may imply a procedure, in which two substances for instance two different fluids or a fluid and a powder are mixed together. After mixing is completed the resulted fluid can be dispensed. Such mixing may be useful, if the resulting fluid may decompose over time.

In an embodiment, the drive assembly or the body of the assembly of the drug delivery device may comprise an element which is adapted to restrict the movement of the button member to be substantially rotational or helical during the transient state. The element may comprise a lug, a projection, a recess, a channel, a guiding track, a combination thereof, or any other element which is able to restrict the movement of the button member. The movement of the button member is restricted before enabling the axial movement. Consequently, the button member can only be displaced in specific and predetermined movements during the pre-ready and transient state and the ready state. The movements in each state are different from each other and may be distinguishable by the user.

The button member may also comprise a guiding element which is in operative connection with a guiding element of the drive assembly or the body. The term guiding element implies an element which may restrict the movement of the button to be substantially rotational or helical during the transient state. Such guiding element may include, but is not restricted thereto, a lug, a projection, a recess, a channel, or a combination thereof. A guiding element of the button member may be in operative connection with the guiding element of the drive assembly or the body. In an embodiment, the guiding element of at least one of the button member, the drive assembly and the body forms a guiding track. The guiding track may comprise a substantially circular or helical shape, thereby restricting the movement of the button to be substantially rotational or helical during the transient state. As a result, the guiding element of the button member engages the respective guiding element of the drive assembly or the body to restrict the movement of the button member during the transient state.

In a further embodiment, the button member may comprise a guiding element being in operative connection with a respective guiding element of the drive assembly or the body, the guiding elements restricting the movement of the button member to a substantial axial movement during the ready state of the drive assembly and the assembly of the drug delivery device.

In an embodiment, the drive assembly may comprise a retaining element adapted in the ready state to prevent the button member from being twisted with respect to the body. The term retaining element implies any element which prevents the button member from being moved in the opposite direction of the movement of the button member during the transient state. For instance, the retaining element prevents the button member from being twisted back with respect to the body after the button member is twisted with respect to the body during the transient state. Accordingly, the retaining element may be adapted in the ready state to prevent the button member from being rotated or from being helically moved.

In another aspect, the button member may comprise the retaining element. The retaining element may comprise a ratchet on the guiding track.

In another embodiment, the drive member may comprise at least one of a moving pivot or a drive sleeve. The term moving pivot implies an element which is restricted to an axial movement within the body for displacing a movable element, for instance the piston rod. The term drive sleeve implies an element which may be arranged between the button and the piston rod. The term drive sleeve may also imply an element comprising a helically shaped surface, said surface engaging, for instance, the body, the piston rod, a lead screw or any other part of the drive assembly. In an embodiment, the drive sleeve may comprise a helically shaped surface which engages a piston rod. In yet another embodiment, the drive sleeve may comprise a helically shaped surface that engages a lead screw nut rigidly fixed to the body of the drug delivery device.

The button member may also comprise a detent to releasably retain the button member in the pre-ready state to prevent an undesired preparation, for instance an undesired priming operation.

In another aspect, a button member for operating a drive assembly of a drug delivery device comprises a first portion being acted upon by a user and a second portion being in operative connection with the drive assembly. The second portion may comprise a first guiding track having a first guiding track portion in a first direction and a second guiding track portion in a second direction. A first guiding track portion is adapted to restrict the movement of the button member to a substantially rotational motion. The second guiding track portion is adapted to restrict the movement of the button member to a substantially axial motion.

As a result, the button member is moved by a user in two different directions in the different states, namely the pre-ready state and the ready state. Such different movements can be easily distinguished by a user and this indicates the state which the assembly of the drug delivery device is in. Accordingly, the first guiding track may act upon a drive assembly or any other portion of the drug delivery device that the button member is part of.

In an embodiment, the button member may comprise a second guiding track, that second guiding track acting upon the drive assembly during the substantially rotational movement of the button member to prepare the drug delivery device. The term prepare implies any operation undertaken upon the drug delivery device which prepares the drug delivery device for later dispense of a desired amount of medicinal product. This may include, but is not restricted thereto, priming the drug delivery device including compensating for any backlashes and tolerances of mechanical parts of the drive assembly and the drug delivery device, closing a gap between a bung and the drive assembly, mixing powder with a fluid to generate the medicinal product and/or expelling a priming portion of the medicinal product or air.

The term second guiding track may comprise a helical shape, a lug, an edge, a recess, a projection, a channel, or a combination thereof. The second guiding track may also comprise a retaining element. The term retaining element implies any element which is adapted to prevent the button member from being reversibly twisted or rotated when the button member is axially moved. The retaining element may comprise a ratchet, the ratchet being in operative engagement with the drive assembly.

The different aspects and features presented above and also presented in conjunction with the accompanying drawings can be combined in different ways without changing the scope of the proposed principle. The embodiments disclosed herein are exemplarily only and not restricted to the specific features as illustrated.

Figure 2:
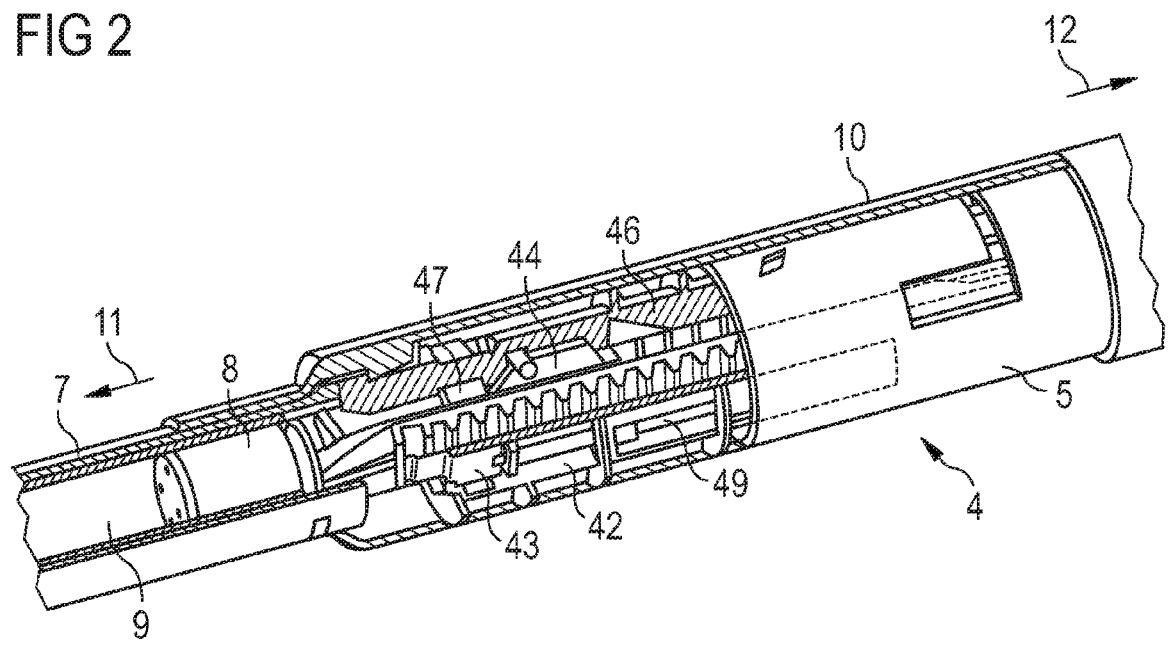
Figure 3A:
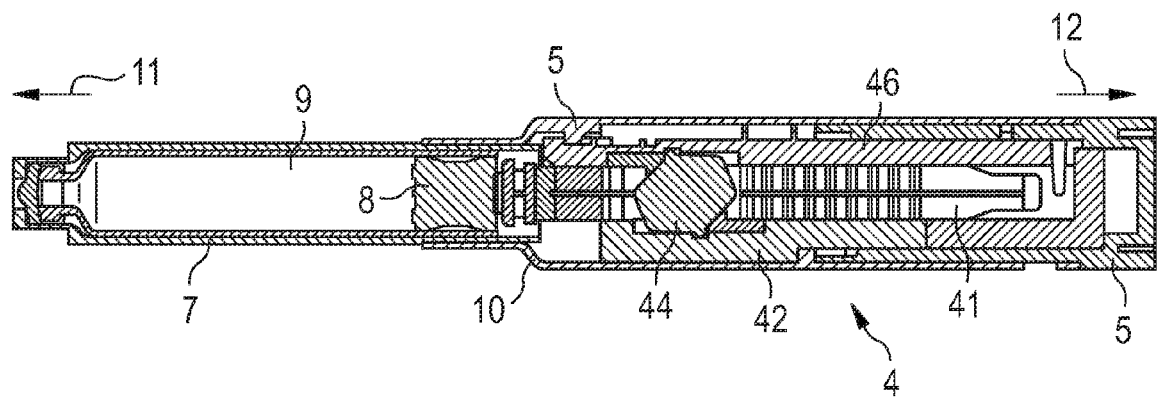
Figure 3B:
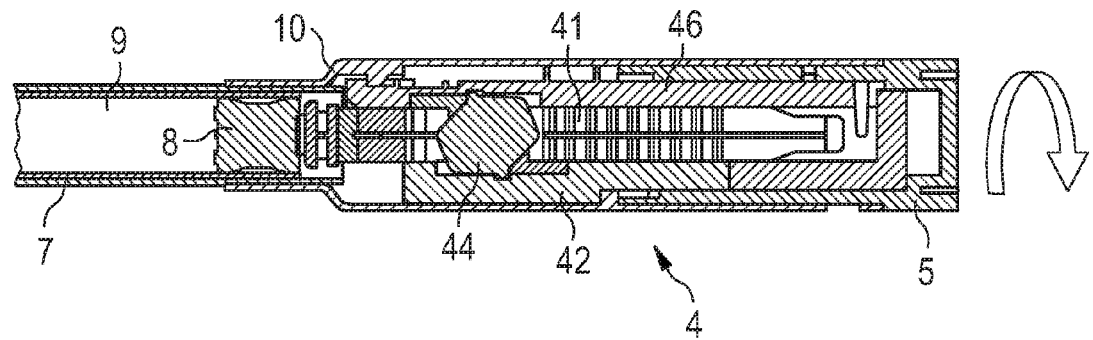
Figure 3C:
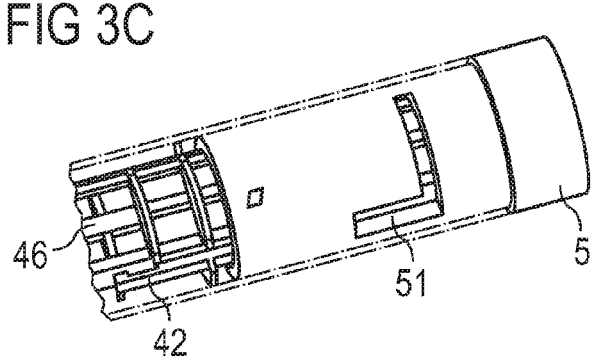
Figure 3D:
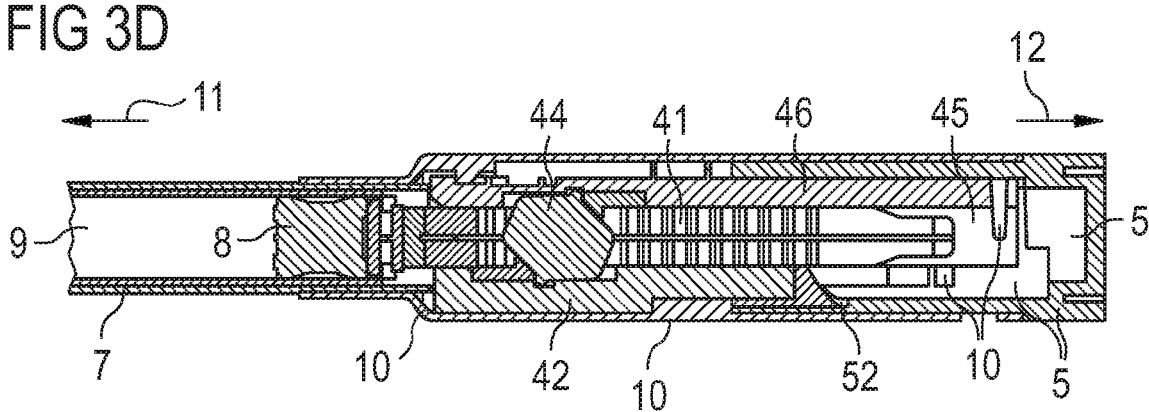
Figure 3E:
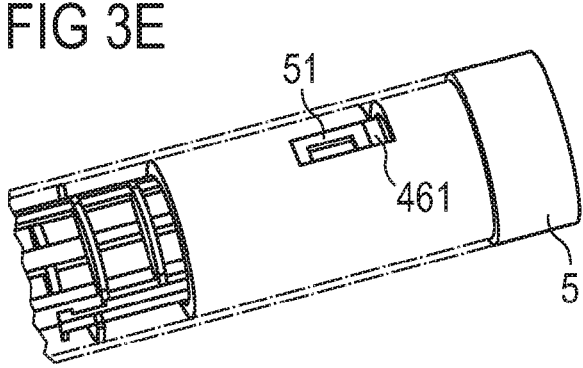
Figure 3F:
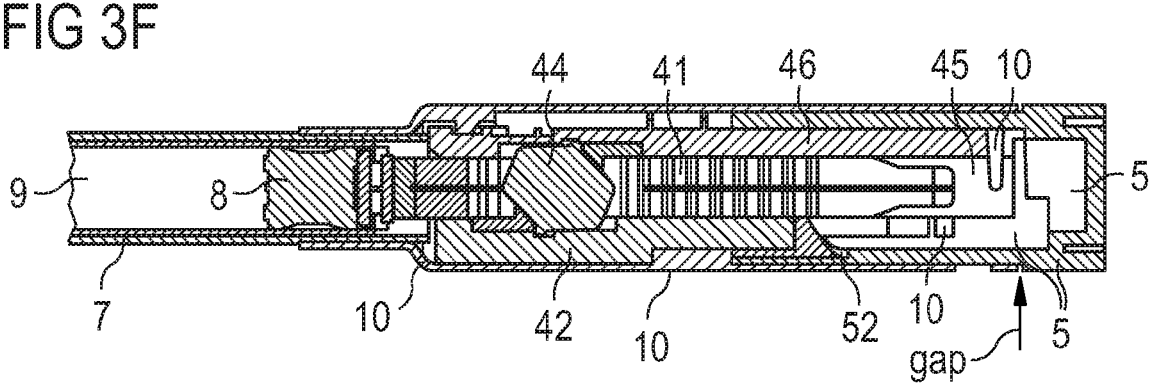
Figure 3G:
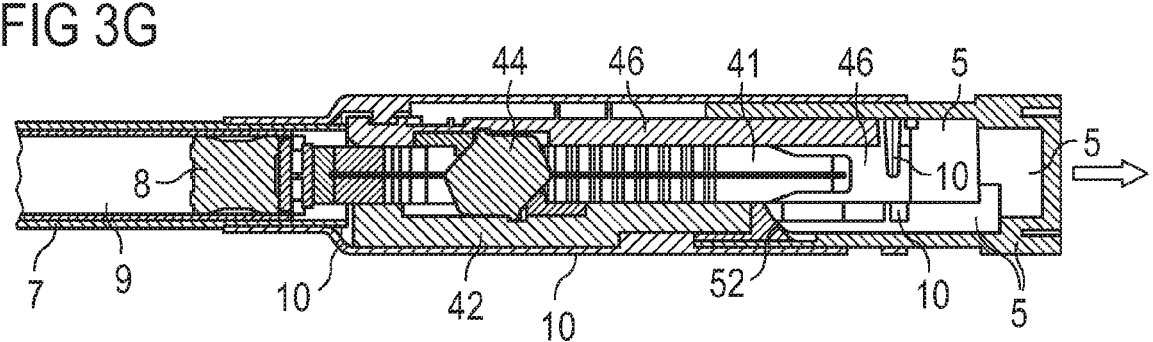
Figure 3H:
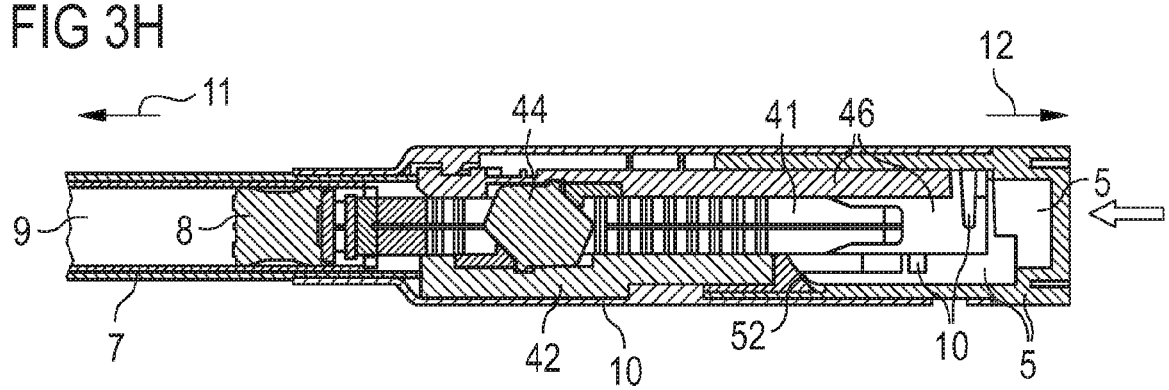
Figure 3I:
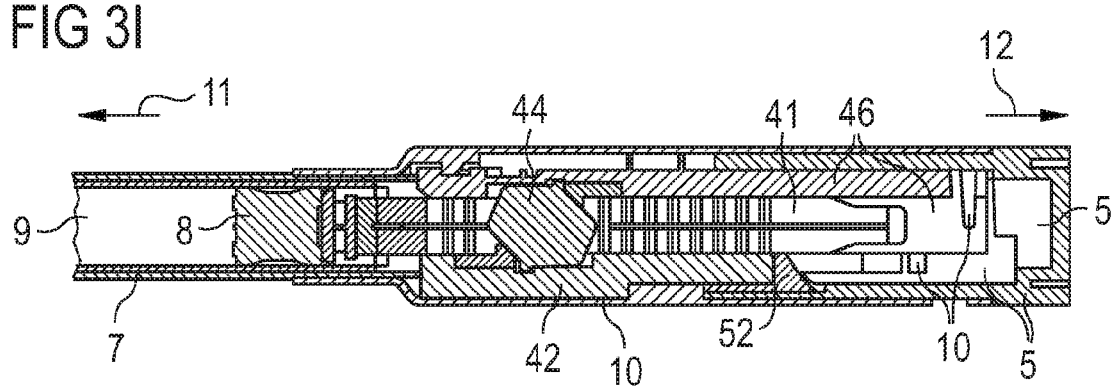
Figure 4:
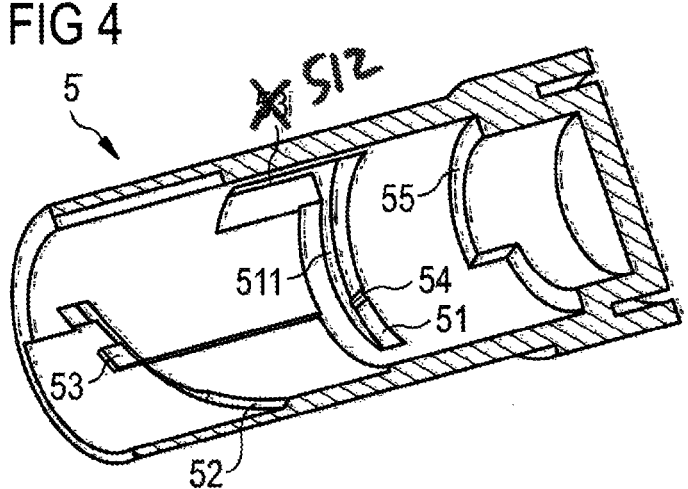
Figure 5:
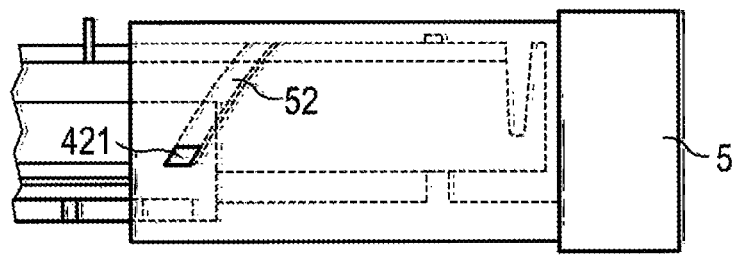
Figure 6:
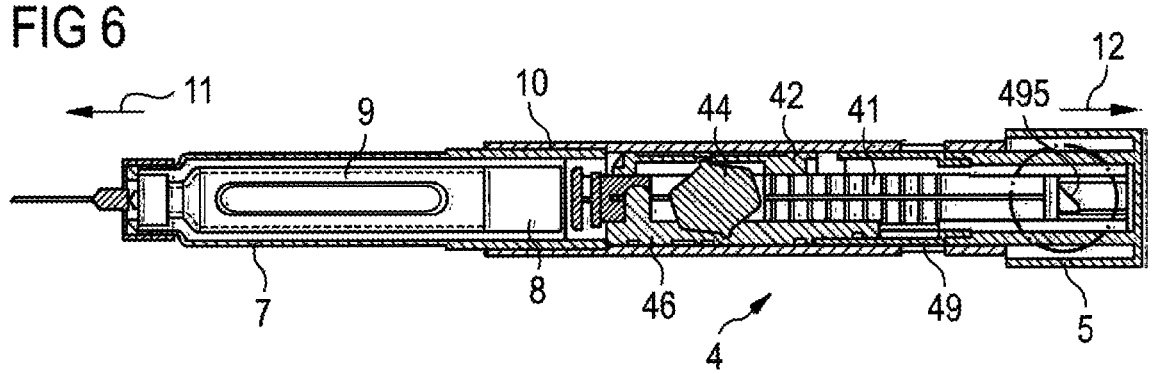
Figure 7:
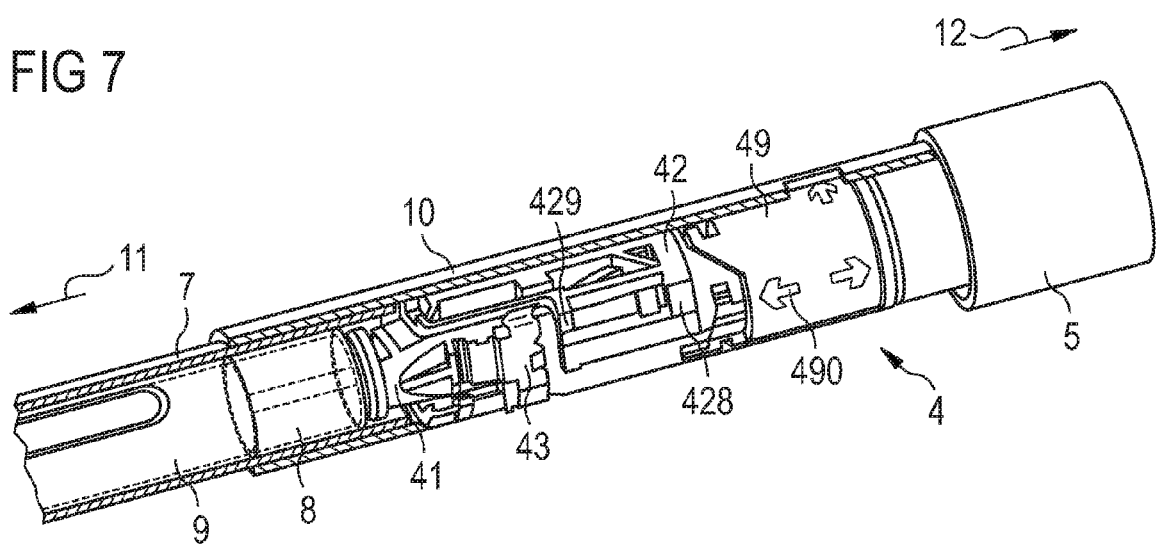
Figure 8A:
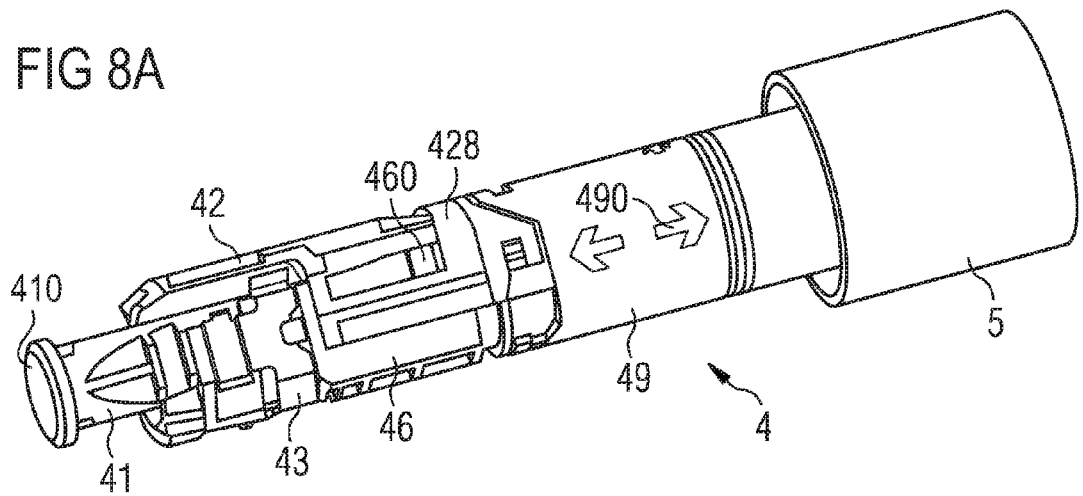
Figure 8B:
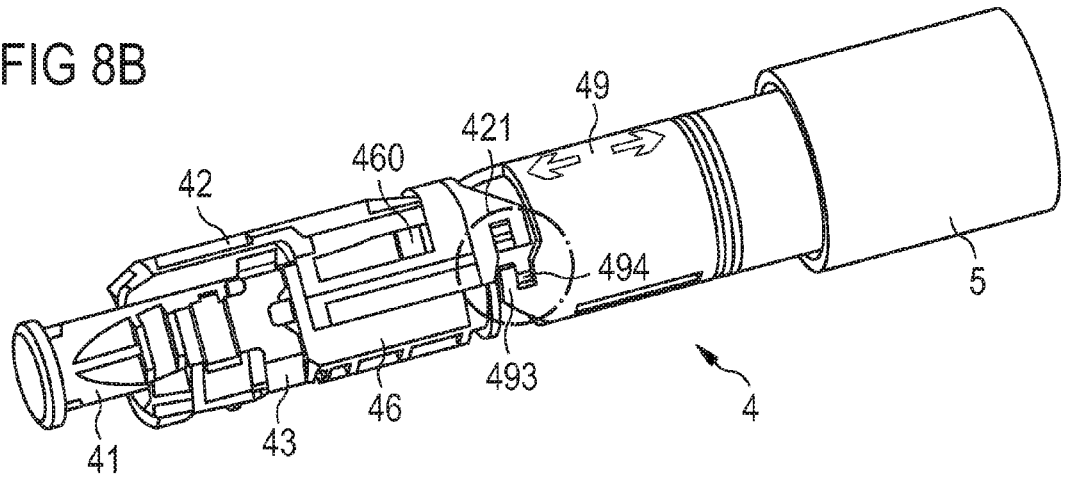
Figure 8C:
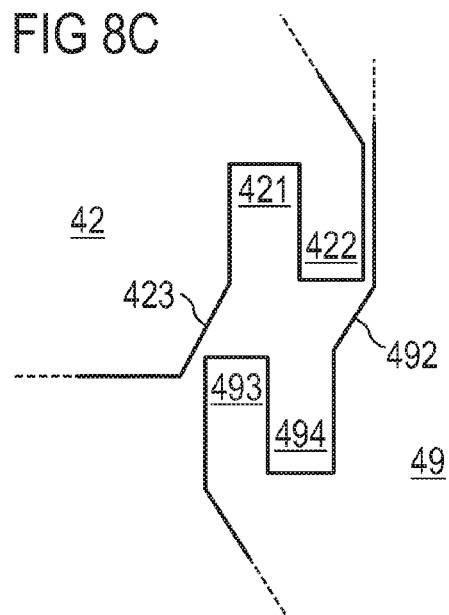
Figure 8D:
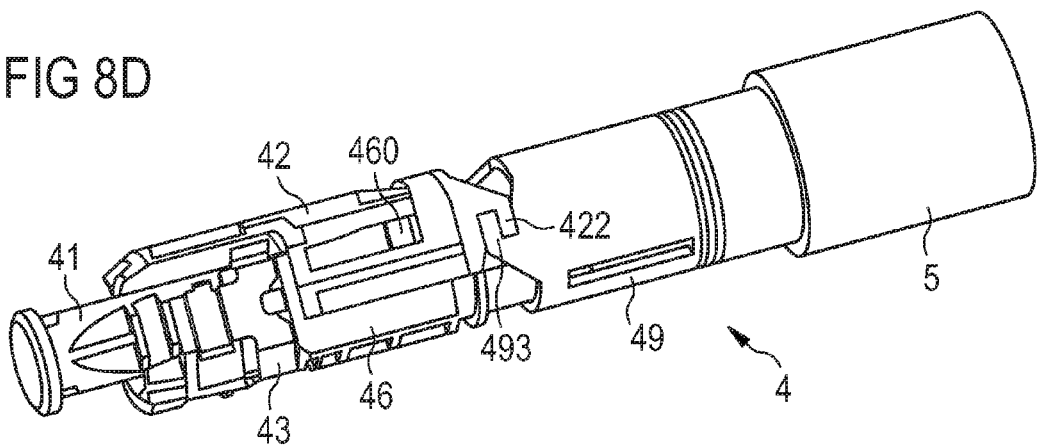
Figure 8E:
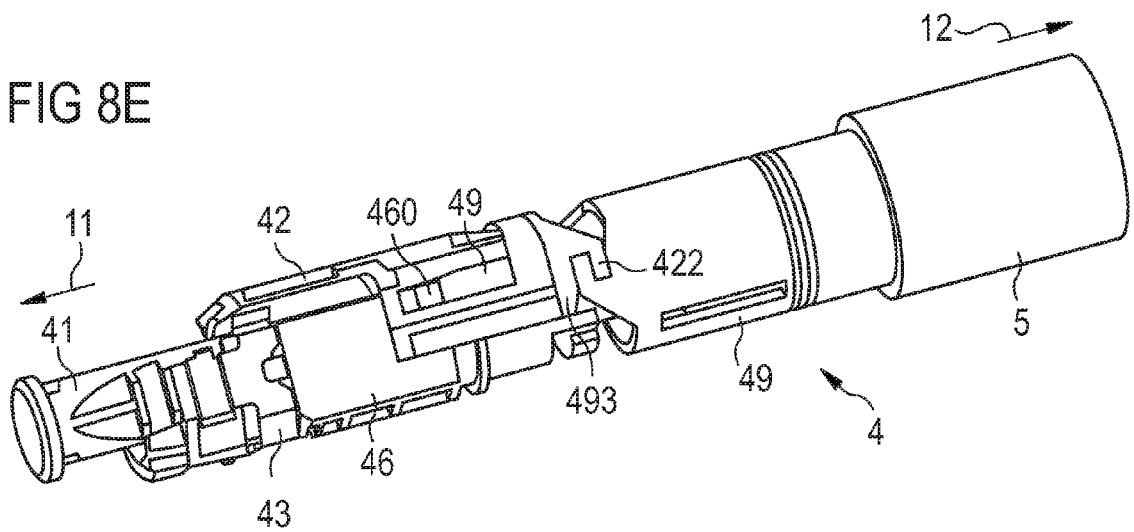
Figure 9:
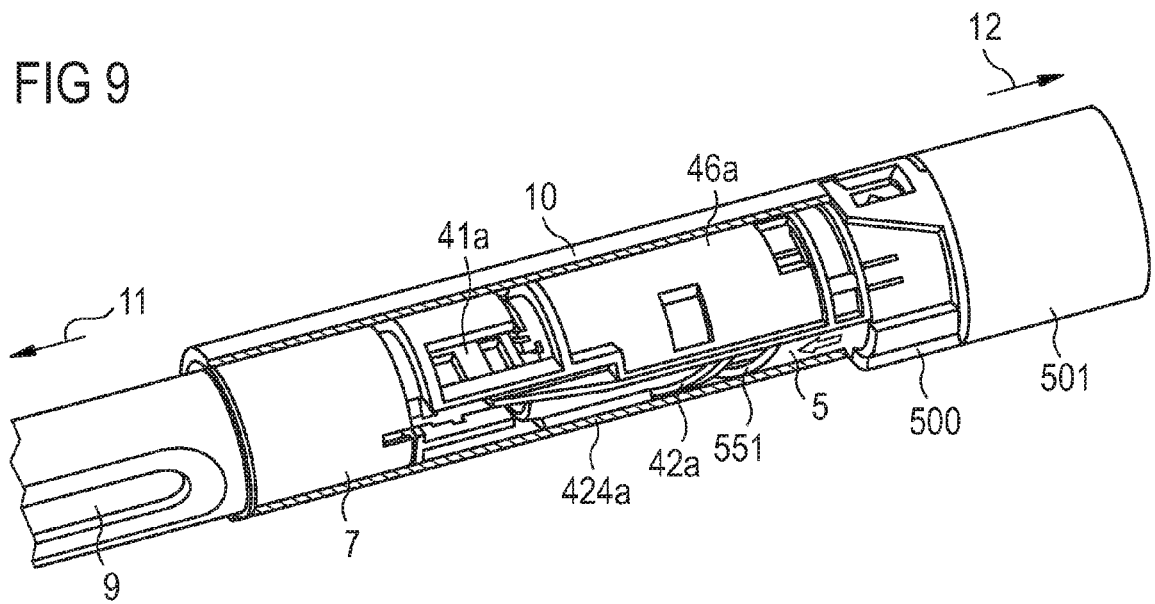
Figure 10:
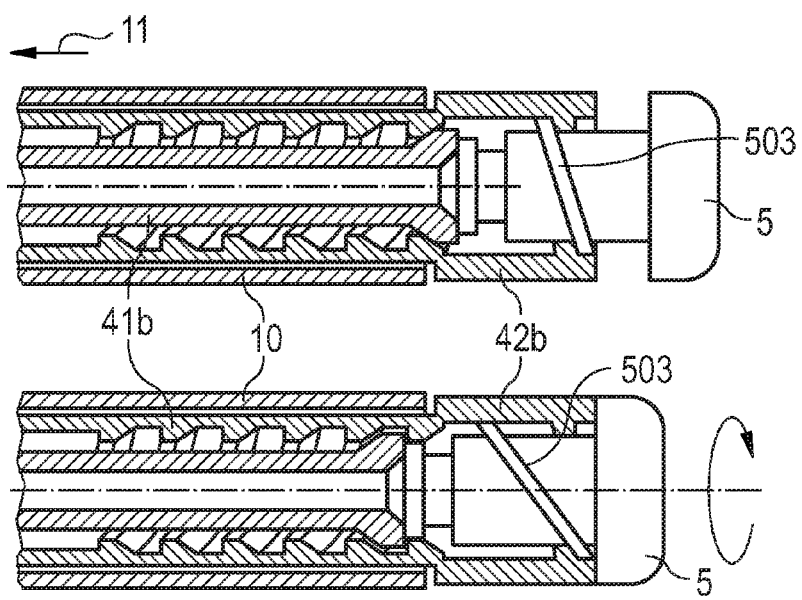
Figure 13:
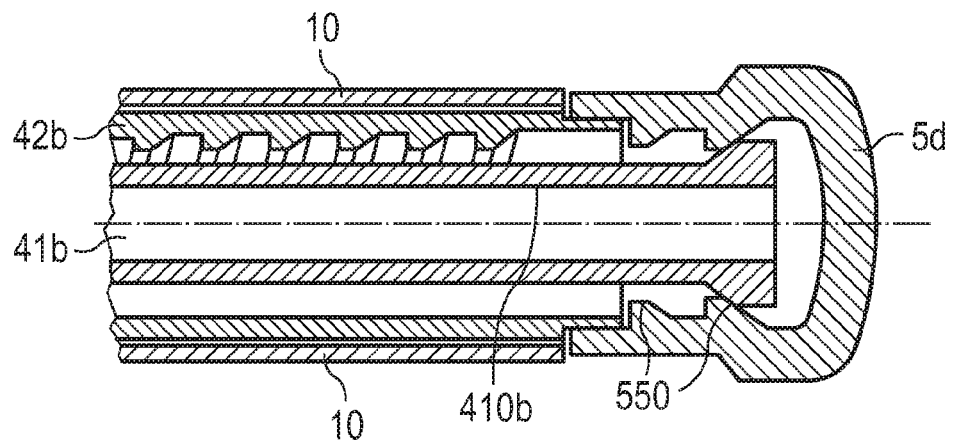
Figure 14:
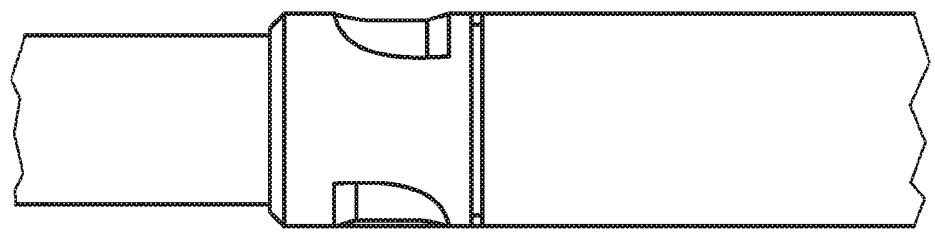
Figure 14A:
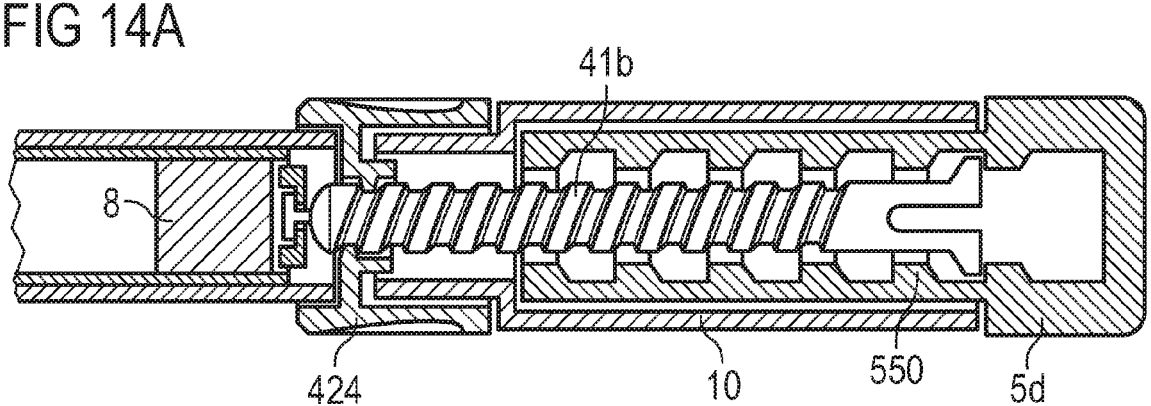

The proposed principle will now be explained in greater detail together with the accompanying drawings in which FIG. 1 illustrates a first embodiment of an assembly of a drug delivery device, FIG. 2 shows a perspective view of the first embodiment, FIGS. 3A to 3I illustrate a cross-section of the first embodiment of the drug delivery device in operating different stages, FIG. 4 illustrates an embodiment of the button member according to an embodiment of the proposed principle, FIG. 5 illustrates the button member in operative connection with some parts of the drive assembly, FIG. 6 shows a cross-section of a second embodiment according to the proposed principle, FIG. 7 illustrates a perspective view of the second embodiment according to the proposed principle, FIGS. 8A to 8E illustrate different operating stages of the second embodiment, FIG. 9 illustrates a third embodiment, FIG. 10 shows a cross-section of a fourth embodiment according to the proposed principle, FIG. 11 shows a fifth embodiment according to the proposed principle, FIG. 12 illustrates a sixth embodiment, FIG. 13 shows a seventh embodiment of a drug delivery device, FIGS. 14, 14A illustrate an eighth embodiment, FIG. 15 illustrates a ninth embodiment according to the proposed principle, FIGS. 16A to 16C show and tenth embodiment of the proposed principle, FIGS. 17A to 17C illustrate the position of a button with respect to the body in different stages according to an embodiment of the proposed principle.

In the following embodiments, some aspects or features may be drawn enlarged with respect to other features. These are for illustration purposes only and may not reflect the real proportions. Similar parts of the different embodiments may comprise the same references.

FIG. 1 shows a first embodiment of an assembly of the drug delivery device illustrating several aspects of the proposed principle.

Assembly 1 comprises body 10 in which the drive assembly of the drug delivery device is arranged. At distal end 11 of assembly 1, a cartridge assembly 9 including cartridge holder 7 and a cartridge is attached. The cartridge assembly 9 comprises a cartridge holder having recesses, in which a respective lugs or projections of body 10 engage, thereby fixing cartridge assembly 9 to body 10.

The drug delivery device further comprises a fixed pivot 46 rigidly fixed to body 10 using clips, of which one close to the distal end 11 is illustrated. A non-return ratchet 43 is attached to fixed pivot 46 and is in operative connection with a piston rod (shown more clearly in FIG. 2). The piston rod is axially movable towards distal end 11 to facilitate dispense of the medicinal product in cartridge assembly 9.

For this purpose, assembly 1 of the drug delivery device also comprises a moving pivot 42, which is in operative connection with the fixed pivot 46 that is attached to body 10. Moving pivot 42 comprises one or more channels 49 which act as guiding track for moving pivot 42 when setting up and dispensing a dose of medicinal product. A lug 460 on the fixed pivot 46 engages channel 49, thereby restraining the movement of moving pivot 42 with respect to fixed pivot 46 and to body 10.

Further, assembly 1 comprises a button 5, which is at least partially arranged within body 10 and in operative connection with the drive assembly and particularly with moving pivot 42. Button 5 is used to set up and dispense a medicinal product during operation of the drug delivery device. In addition, button 5 is used to prepare the drive assembly including moving pivot 42 and piston rod 41. In this respect, preparing the drug delivery device indicates and includes every operation which prepares the drug delivery device and the drive assembly for setting up and dispensing a dose of a medicinal product. Preparing may for instance include priming.

Button 5 comprises channel 51 acting as guiding track for the button during any preparation operation as mentioned above as well as during the ready-state operations including setting up and dispensing a dose of medicinal product. Channel 51 comprises a first channel portion 511 which is substantially arranged in axial direction of the drug delivery device and a second portion 512 arranged perpendicularly thereto. Pre-ready-state operation as well as setting up and dispensing a dose of medicinal product using button 5 will be explained in greater detail in accordance with FIGS. 3A to 3I.

FIG. 2 shows a cross-section through the assembly according to the embodiment of FIG. 1. Piston rod 41 comprises a plurality of engagement members implemented as teeth-like structure, which engage non-return ratchet 43 firmly attached on fixed pivot 46. Non-return ratchet 43 prevents a movement of piston rod 41 towards the proximal end 12 of the drug delivery device. Bung 8 is arranged in cartridge holder 7 between piston rod 41 and a cartridge containing the medicinal product. By moving piston rod 41 towards distal end 11, piston rod 41 acts on bung 8 to dispense the medicinal product. The dose dispensed by such movement is substantially defined by the movement of piston rod 41. Piston rod 41 is in turn driven by moving pivot 42 in connection with lever 44, both of them acting as drive members for piston rod 41. During set-up and dispense of the drug delivery device, button 5 is axially moved towards proximal direction 12 for setting up a dose and towards distal direction 11 for dispensing the respective dose of the medicinal product. During setting up of the dose, button 5 acts upon moving pivot 42 and lever 44 as long as the movement of moving pivot 42 is not restrained by the lug 460 on fixed pivot 46.

FIGS. 3A to 3I illustrate the pre-ready and transient operation for preparing the drug delivery device for dispensing a medicinal product as well as setting up a dose to be dispensed and dispensing that dose. FIG. 3A shows the cross-section of the drive assembly according to the embodiments of FIG. 1 and FIG. 2. Drug delivery device 1 includes a body 10 in which drive assembly 4 is arranged. Drive assembly 4 comprises inter alia moving pivot 42, lever 44 as well as piston rod 41. Moving pivot 42 and lever 44 may act on piston rod 41 during the transient state of the drug delivery device as well as during the ready states for setting up and dispensing a dose of medicinal product.

At the distal end of body 10, a cartridge assembly 9 including cartridge holder 7 and bung 8 is secured to body 10. Cartridge assembly 9 may comprise a cartridge including the medicinal product. In the initial state, the drug delivery device according to this embodiment has a gap between piston rod 41 and bung 8 of cartridge assembly 9, due to manufacturing tolerances of the drug delivery device and the desire not to apply pressure to the bung in a storage condition. This gap would cause inaccuracy when dispensing the first dose of a medicinal product and it must therefore be closed before delivering the first dose. It is therefore necessary to prepare drive assembly 4 of the drug delivery device accordingly, before setting up and dispensing the first dose of the medicinal product.

Moving pivot 42 comprises a small recess in which a projection of lever 44 engages. Lever 44 is rotated when the moving pivot 42 is moved in either a distal or a proximal direction. In addition or also alternately, fixed pivot 46 may also comprise a recess to engage lever 44.

FIG. 3B illustrates the initial pre-ready state, in which button 5 is only twistable with respect to body 10, but not axially movable. During rotation of button 5, as indicated in FIG. 3B, drive assembly 4 is being prepared for setting up and dispensing a dose. Backlashes and tolerances between the different parts of drive assembly 4 are compensated. Further, the gap between bung 8 and piston rod 41 is closed.

FIG. 3C shows a side view of button 5 including channel 51 and fixed pivot 46 as well as moving pivot 42 during the initial state of the drug delivery device in greater detail. In the initial state, the channel 51 defines that the button 5 is only twistable, and in particular rotatable, perpendicular to the distal and proximal directions of the drug delivery device. Button 5 can be rotated perpendicular to the longitudinal axis of the drug delivery device, but not axially moved.

FIG. 3D shows the transient state, in which preparing the drug delivery device for later setting up and dispensing a dose is conducted. During the transient state, button 5 is rotated as indicated in FIG. 3B, thereby acting upon moving pivot 42 and lever 44 as illustrated. Button 5 comprises a helically shaped track 52 acting on moving pivot 42 to move pivot 42 towards distal end 11. As lever 44 is coupled with its projection into the recess of moving pivot 42, it is partially rotated as indicated. Any tolerances between lever 44 and moving pivot 42 are compensated by such movement.

Further, moving pivot 42 is in operative connection with piston rod 41. Accordingly, the rotational movement of button 5, acting upon moving pivot 42 and drive lever 44 to drive piston rod 41 towards distal end 11, thereby closing the gap between bung 8 and piston rod 41. Depending on the movement of piston rod 41, a small amount of medicinal product may be expelled.

FIG. 3E illustrates the position of button 5 with respect to drive assembly 4 including moving pivot 42 and fixed pivot 46. In this specific embodiment, some specific features on button 5 act upon fixed pivot 46 and further restrict the movements of button 5 to a pure rotational movement for preparing the drug delivery device and a pure axial movement for setting up and dispensing the desired doses of fluid. The rotation of button 5 is restricted to a purely rotational movement during the priming step and a purely axial movement during the dose setting and delivery steps by the interaction of the feature 461 of fixed pivot 46 acting within the guide channel 51 of the button. There is a ratchet between the button and moving pivot which prevents the button being rotated in reverse after the preparing step has been completed.

As shown in FIG. 3C lug 461 is not at a position within channel 51, which allows an axial movement of button 5.

FIG. 4 shows a cross-section illustrating several aspects of button 5. Button 5 comprises, as already illustrated in FIGS. 1 and 2, a channel 51 in the shape of an L having a first portion 511 and a second portion 512. A small detent 54 arranged in first channel portion 511 of channel 51 prevents button 5 from being accidentally rotated. Channel portion 511 is substantially arranged perpendicular to the longitudinal axis of the drug delivery device, while channel portion 512 is parallel to the longitudinal axis of the drug delivery device. A lug on the fixed pivot (not shown herein) engages channel 51 to restrict the movement of button 5 either to a rotational movement in channel portion 511 or to an axial movement in channel portion 512.

Button 5 also comprises helical track 52 acting on moving pivot 42. A non-return ratchet 53 is arranged on the helical track to retain any movement of moving pivot 42 after the preparing steps are completed. For this purpose, moving pivot 42 also comprises a small projection 421 engaging the helical track 52 of button 5.

During preparing the drug delivery device for setting up and dispensing a dose of medicinal product, button 5 is rotated and the lug 461 of fixed pivot 46 is moved along first channel portion 511. Due to the rotation, helical track 52 acts upon projection 421 on moving pivot 42, thereby driving moving pivot 42 axially in the distal direction. The operation drives the main mechanism to close the gap between bung 8 and piston rod 41 as well as expel a priming amount of the medicinal product. During the rotational movement, helical surface 55 engages and compresses a back-off spring part of fixed pivot 46.

FIG. 5 illustrates an end position of button 5 after preparing the drug delivery device has been completed. The back-off spring on fixed pivot 46 is compressed and recess 421 on moving pivot 42 snaps into the recess at the end of first helical track 52 of button 5. Non-return ratchet 53 at the end of the first helical track 52 prevents any rotational movement of button 5 in the reverse direction. At the same time, lug 461 on fixed pivot 46 has reached second channel portion 512, thereby allowing an axial movement of button 5. As soon as the user releases button 5, the compressed back-off spring may be slightly relieved, thereby driving button 5 a small distance in the proximal direction.

The position of button 5 with respect to body 10 after the back-off has occurred by the action of the back-off spring on fixed pivot 46 is illustrated in FIG. 3F. A small gap between button 5 and body 10 at the proximal end indicates the back-off position at the end of the transient state and in the ready state. The back-off position corresponds to a position, in which the drug delivery device is kept while it is not in use. The back-off position relieves any stress on the mechanical parts of the drive assembly and bung 8, but without generating backlashes or tolerances in between, which have been compensated during the preparing procedure in the transient state.

FIG. 3F therefore indicates the ready state, in which the drug delivery device is fully prepared for setting up and dispensing the desired dose of medicinal product. The non-return ratchet 53 now retains the moving pivot 42 such that the moving pivot 42 and button 5 are rigidly and permanently attached. Button 5 cannot be rotated after the non-return ratchet has snapped over projection 421 of the moving pivot 42. A user is thereby prevented from moving the button in anything other than an axial direction.

For setting up a dose button 5 is moved in the proximal direction as indicated in FIG. 3G. As button 5 is in operative connection with moving pivot 42, a movement of button 5 also moves pivot 42 towards the proximal end of the drug delivery device. At the same time, lever 44 is rotated towards its first position. After setting up the dose to be dispensed, button 5 can be pushed towards distal end 11 of the drug delivery device as indicated in FIG. 3H. Accordingly, moving pivot 42 is driven towards distal end 11, thereby acting upon piston rod 41 to drive piston rod 41 in the distal direction 11. After the dose has been dispensed, the back-off spring of fixed pivot 46 acts upon button 5 to remove the pressure from bung 8 when the button is released at the end of the dispensing operation.

The specific structure of button 5 including the several lugs on fixed pivot 46 as well as on moving pivot 42 provides a pure rotational movement of button 5 during the pre-ready and the transient state while preventing such movement as soon as preparation is completed and the drug delivery device is in the ready state. In the ready state, button 5 can be moved only in an axial direction, when both setting up and dispensing a dose.

FIG. 6 shows a second embodiment of a drug delivery device providing a rotational or helical movement for preparing the drug delivery device for setting up and dispensing a dose and an axial movement for setting up and dispensing the dose. These different allowable movements indicate the current state of the drug delivery device to a user. The drug delivery device in this embodiment comprises a body 10, in which the drive assembly 4 is arranged. At the distal end of body 10, cartridge assembly 9 including a cartridge, cartridge holder 7 and bung 8 is rigidly attached. A small gap exists between bung 8 and piston rod 41 of drive assembly 4 before the drug delivery device has been prepared for setting up and dispensing a dose. This gap is a result of manufacturing tolerances in the drug delivery device and the desire not to compress the bung during storage.

Drive assembly 4 comprises a fixed pivot 46 rigidly attached to body 10, moving pivot 42 as well as lever 44 and non-return ratchet 43. Piston rod 41 is in operative connection with moving pivot 42. Further, piston rod 41 comprises a helically shaped surface at its proximal end which engages a respectively shaped surface 495 of drive sleeve 49. Drive sleeve 49 is permanently coupled to button 5 by a closing plate (not shown in this cross-section view).

For preparing the drug delivery device to set up and dispense a medicinal product, button 5 and drive sleeve 49 are rotated. Accordingly, the helically shaped surface 495 of drive sleeve 49 acts upon the respective helically shaped surface of piston rod 41 to displace piston rod 41 into distal direction 11, thereby closing the gap between bung 8 and piston rod 41.

FIG. 7 shows a perspective sectioned view of the embodiment according to FIG. 6.

Drive sleeve 49 also has different markings indicating the direction in which button 5 can be moved to a user. In this embodiment, a first arrow indicates a rotational movement of button 5, while two arrows 490 pointing in opposite directions indicate an axial movement for setting up and dispensing the medicinal product. During the different operation of the drug delivery device, the arrows are visible through a window aperture in body 10. Drive assembly 4 comprises a fixed pivot 46 having at least one lug 460, which engages a channel of moving pivot 42. The channel is formed between two webs 428 and 429, thereby restraining the movement of moving pivot 42 during the setting and dispense operation of the drug delivery device. A non-return ratchet 43 is attached to fixed pivot 46 and in operative connection with piston rod 41. For that purpose, piston rod 41 comprises teeth-like structures engaging the non-return ratchet 43. Ratchet 43 prevents displacement of piston rod 41 in the proximal direction.

FIGS. 8A to 8D illustrate several positions during the pre-ready and the transient state when preparing the drug delivery device for setting up and dispensing a dose of the medicinal product.

FIG. 8A shows the drive assembly in the pre-ready state. Arrows 490 pointing in different directions indicate movement of button 5 during the different operating states of the drive assembly 4. Arrows 490 are marked on drive sleeve 49 by printing, laser marking, moulding or other means. Of course different markings can be used instead of arrows. In the pre-ready state, a single arrow, pointing in a direction substantially perpendicular the longitudinal axis of the drug delivery device is visible through the aperture in body 10 (body 10 is not shown herein for convenience purposes). The arrow indicates the possible movement of button 5 in the pre-ready state to a user. In the pre-ready state, drive sleeve 49 is disconnected from moving pivot 42. Moving pivot 42 is in a position in which the lug 460 on fixed pivot 46 is close to touching the upper right web 428 of moving pivot 46. Non-return ratchet 43 prevents the piston rod 41 from moving in a proximal direction.

For preparing the drive assembly for setting up and dispensing a dose, button 5 is rotated as indicated by the arrow in the aperture of body 10. As button 5 is rigidly fixed to drive sleeve 49, drive sleeve 49 is rotated as well. During the rotation, a ramped interface of drive sleeve 49 on its distal end comes into view as illustrated in FIG. 8B. The interface fits into a respective ramped interface on moving pivot 42. The ramped interface on drive sleeve 49 comprises an outer projection 493 and an inner recess 494 both of which fit into a respective recess 421 and projection 422 of moving pivot 42. This structure on moving pivot 42 also exists on the other side of moving pivot 42. Accordingly, a further set of ramped interface features of drive sleeve 49 also exist on the other side; such that the drive sleeve 49 is symmetrical in this respect.

A more detailed view of the ramped interface structure can be seen in FIG. 8C. Moving pivot 42 comprises a slightly slanted surface 423 neighboring the recess 421 of moving pivot 42. A projection 422 is arranged next to the recess 421. A similar structure is arranged on drive sleeve 49 including recess 494 arranged neighboring to a slanted surface 492. A projection 493 on the outer side of drive sleeve 49 fits into recess 421 of moving pivot 42. Both slanted surfaces 423 and 492 act as a guidance when drive sleeve 49 is rotated to engage projections 493 and 422 in the respective opposite facing recesses.

When the device is prepared, the piston rod is initially moved in the distal direction by the interaction of the helical shaped surface 495 of drive sleeve 49 with the corresponding helical surface at the extreme proximal end of the piston rod. This movement advances the piston rod towards the bung and engages the piston rod with the carrier plate to which the lever is attached. Then towards the end of the rotational movement of the button, the drive sleeve starts to engage with the moving pivot (as described above). The ramp features 423 and 493 push the moving pivot in the distal direction, thus rotating the lever and to take up all tolerances and advance the piston rod a little further (thus priming the device). This double operation has a major advantage over the first embodiment in that it is possible to have a much smaller rotation of the dose button (i.e. 90 degrees).

As soon as projections 493 and 422 snap into the respective recesses, a non-return ratchet (not shown) which may be part of the moving pivot 42 snaps to the drive sleeve, thereby preventing rotation of a drive sleeve 49 in the reverse direction.

To further indicate the pre-ready, the transient and ready states of the drug delivery device according to the embodiments of FIGS. 7 and 8, button 5 is shaped not circular but oval. Of course, a different regular shape can be used as well. The oval shape may correspond with a respective oval shaped structure on the surface of body 10 indicating a misalignment or alignment of a button 5 with respect to the body. Such misalignment may indicate the user whether the drug delivery device is in the pre-ready or the transient state or in the ready state. For instance, as indicated in FIGS. 8A, 8B and 8D, the regular shaped button 5 is rotated during preparation of a drug delivery device. As soon as the drug delivery device reaches the ready state as indicated in FIG. 8D, the oval shape of button 5 is aligned with a respective shaped structure on body 10 of the drug delivery device indicating to the user that the ready state of the drug delivery device has been reached.

During set and dispense operation as indicated in FIG. 8E, button 5 coupled to drive sleeve 49 is axially moved in proximal and distal direction, respectively. For setting up the dose to be dispensed, button 5 is moved along a proximal direction, thereby also taking moving pivot 42 along due to projections 422 and 493 engaging the respective recesses. Lug 460 on fixed pivot 46 restraints the movement of moving pivot 42 as soon as it reaches the web 429 at the distal end of channel 49 of moving pivot 42. The drug delivery device is set up and ready for dispensing a dose. In this position, drive assembly 4 is ready to displace and drive piston rod 41 towards the distal end of the drug delivery device upon pushing button 5 in the distal direction. Again, non-return ratchet 43 prevents movement of piston rod 41 when setting up the dose, particularly when the moving pivot 42 and drive sleeve 49 are moved in a proximal direction.

An aperture in body 10 of the drug delivery device at the position of the arrows on the drive sleeve 49 also indicate to a user the respective possible movement directions of button 5. In the pre-ready state and the beginning of the transient state, the arrow indicating the rotational movement is visible in the window in body 10. Upon rotating button 5 during the transient state, the respective arrow disappears from view in the window and one of arrows 490 comes into view. At the same time, the misalignment between button 5 and the respective oval shaped portion of body 10 is corrected and as soon as the ready state of the drug delivery device has been reached, button 5 and the respective oval portion of body 10 are perfectly aligned.

An embodiment indicating the different operating states due to misalignment between button 5 and body 10 can be seen in FIG. 17A to FIG. 17C.

In this embodiment, body 10 comprises an oval structured surface similar to the structure of button 5. Further, button 5 comprises a first part 32 of a pattern at its distal end facing body 10. Body 10 comprises a second part 34 of the pattern at its proximal end. If both parts are aligned to each other they form a cross X.

However, as shown in FIG. 17A, button 5 and body 10 are misaligned in the pre-ready state. At the same time, the first part 32 on button 5 of the pattern is misaligned with respect to the second part 34 on body 10. An arrow pointing towards the left side is shown in window 101 indicating the user the possible movement direction of button 5. In this embodiment, button 5 can only be rotated in the direction indicated by the arrow shown in the window.

During the procedure of preparing the drug delivery device for setting up and dispensing an amount of a medicinal product, the button is rotated and slowly becomes aligned with body 10. FIG. 17B illustrates the transient state during which the button is rotated. As the button rotates, the misalignment between first part 32 of the pattern on button 5 and second part 34 on body 10 decreases. The misalignment between body 10 and button 5 also decreases. At the same time, the arrow in window 100 disappears and one of the arrows 490 indicating the set operation comes into view in window 101 of body 10. At the end of the transient state, preparing is completed and the drug delivery device is in the ready state, prepared for setting up and dispensing a dose. Button 5 is perfectly aligned with body 10 as indicated in FIG. 17C. Both parts 32 and 34 on button 5 and body 10, respectively form a cross also indicating an alignment. Arrow 490 indicates the only possible movement of button 5. Afterwards a dose of medicinal product can be set by moving button 5 towards the proximal direction, after which a new arrow indicates the respective possible movement of button 5 to dispense the previously set up dose.

FIG. 9 illustrates a further embodiment showing several aspects of the proposed principle. In this embodiment, the mechanism is for preparing the drug delivery device to set and dispense a dose. Drive assembly 4 comprises a drive sleeve 42a, a lead screw 41a to drive a bung within cartridge assembly 9 towards the distal end of the drug delivery device. Cartridge assembly 9 is firmly attached by cartridge holder 7 onto body 10 of the drug delivery device.

The drug delivery device further comprises button 5 and button finisher 501, both of them permanently and rigidly fixed together. If button 5 and button finisher 501 are producable, they can be implemented by a single component. Button 5 and button finisher 501 act upon drive sleeve 42a, which in turn drives lead screw 41a towards a distal direction.

Lead screw nut 46a is permanently and rigidly mounted to body 10. Axial movement of Drive sleeve 42a in the distal direction drives the lead screw also towards the distal end for preparing the drug delivery device to set up and dispense a dose of medicinal product. The permissible movement of the drive sleeve is restricted to a limited axial movement by features that interact between the drive sleeve and the lead screw nut 46a.

During the pre-ready and the transient state, button 5 can rotate relative to drive sleeve 42a. In particular, button 5 is restricted to rotation by features that interact either between button 5 and body 10 or between button 5 and lead screw nut 46a. Button 5 is restricted to rotation until the preparation procedure has been completed, after which only an axial movement for setting up and dispensing a respective amount of medicinal product is possible. As previously mentioned, preparing the drug delivery device may include a prime step, including but not limited to expelling a prime amount of fluid. The preparation procedure may further include compensating all backlash and tolerances between the different mechanical parts, including closing a gap between lead screw 41a and bung within cartridge holder 7. It may also comprise a step of mixing a first medicinal product with a second medicinal product, for instance a powder with a fluid.

Drive sleeve 42a comprises a helically arranged projection 424a which engages a respective helically shaped surface 551 on button 5. During the preparation step, as the button 5 is rotated relative to the drive sleeve the helical surface on button 5 acts upon drive sleeve 42a and particularly on the projection 424a, axially driving sleeve 42a in the distal direction 11. Drive sleeve 42a acts upon lead screw 41a causing the lead screw to rotate and thus to advance in the distal direction as well by means of a threaded connection between the lead screw 41a and lead screw nut 46a. The movement of lead screw 41a closes any gap between lead screw and the bung in the cartridge holder and may also expel an amount of prime fluid.

At the end of the rotation of button 5 and button finisher 501, button 5 and drive sleeve 42a snap together such that the components are rigidly and permanently attached to each other. At this time, only an axial movement of button 5 and button finisher 501 in distal and proximal directions is possible for setting up and dispensing the respective doses of medicinal product.

Further embodiments illustrating the principle of rotating or twisting the button 5 to prepare a drug delivery device or the drive assembly within the drug delivery device to set up and dispense a dose are illustrated in FIGS. 10 to 16.

The embodiment according to FIG. 10 comprises a button 5 having a helically shaped projection 503. The projection 503 directly acts on drive member 41b, in this case a lead screw, thereby driving the lead screw towards the distal end. At the end of the twist action, button 5 acts on drive sleeve 42b in which any tolerances between drive sleeve 42b, button 5 and drive sleeve 42b and lead screw 41b are compensated. Further, drive sleeve 42b and button 5 snap together and are now permanently and rigidly attached to each other. Drive sleeve 42a comprises a wedge shaped thread form, which engages the lead screw 41b to drive lead screw 41b towards the distal end during dispensing a dose.

FIG. 11 illustrates another embodiment of a drive assembly of a drug delivery device. The drug delivery device in this embodiment comprises a rotatable collar 505 arranged between button 5 and body 10. Collar 505 comprises projections 506 facing inwards and engaging open ended slots on the proximal end of lead screw 41b. The open ended slots on the proximal end of lead screw 41b are helically shaped such that during rotation of collar 505, lead screw 41b is driven towards the distal end until the projections 506 come out of engagement with the lead screw. When this position is reached, projection 506 will not engage the slots anymore. A small retaining element is arranged at the proximal end closing the slots in lead screw 41b, so that if collar 505 is rotated in reverse direction, the projections 506 do not re-engage the slots in the lead screw.

During the advancement of the lead screw 41b, any backlashes or tolerances between lead screw 41b and the bung within the cartridge are compensated. Further, the advancement of the lead screw can be selected such that a small amount of priming fluid is expelled.

A slightly different embodiment is illustrated in FIG. 12, in which button 5b is coupled to lead screw 41c using several splines 508. Splines 508 are arranged on the inner sidewalls of button 5b and engage respective guiding tracks in lead screw 41c. When the button 5b is rotated, lead screw 41c also rotates and advances in distal direction due to a threaded engagement between the lead screw and the housing. During the advancement, the drive assembly of the drug delivery device is prepared for setting and dispensing a respective dose of medicinal product. At the end of the advancement of lead screw 41c, splines 508 of button 5 disengage from the respective guiding tracks on lead screw 41c such that a lead screw 41c can be driven towards the distal end by axially moving button 5b, operatively connected to drive sleeve 42b. Again, a retaining element may be arranged at the proximal end of lead screw 41c.

FIG. 13 shows a further embodiment. In this embodiment, button 5d comprises an inner cylindrical surface having some threads, similar to those of the drive sleeve 42b. By rotating the button, lead screw 41b is driven and also rotates due to the thread 550 on the inner sidewall of button 5d engaging a helical surface at the proximal end of the lead screw. At the end of the rotation of the button, the thread in the button aligns with the thread on the internal surface of the drive sleeve 42b and both components snap together. The rotation of button 5b causes the lead screw 41b to be driven towards the distal end due to a threaded engagement between the lead screw and the housing. The displacement of lead screw 41b stops as soon as the rotation of button 5d is stopped.

An exterior view of a further embodiment is illustrated in FIG. 14. A collar 424 is arranged distal to button 5d. The externally arranged collar 424 comprises additional marking on the outer surface indicating an operation to be performed as a next step. For instance, the indication on the collar or the button comprise some misalignment with respect to the body indicating to the user to rotate the collar until the markings on the button are aligned with respective markings on the body.

In this embodiment, the lead screw nut, which is normally rigidly and permanently attached to the body, is movable in the pre-ready and during the transient state. By rotating the button or a collar which is operatively coupled to the lead screw nut, the lead screw nut is rotated, thereby displacing the lead screw towards the distal end by means of a threaded connection between the lead screw and lead screw nut. Accordingly, the drive assembly is prepared for setup and dispense of a dose of a medicinal product. At the end of the preparation procedure, corresponding to the end of the transient state, the lead screw nut attaches permanently and irreversibly to the body. At the same time, the button is released such that the first dose can be set by axially moving the button in the proximal direction. By pushing the button into distal direction, the button acts on the drive assembly to dispense the previously set amount of medicinal product.

In a slightly different embodiment as illustrated in FIG. 14A, collar 424 engages and is in operative connection with lead screw 41b, by rotating collar 424, lead screw 41b is rotated as well and at the same time moved towards bung 8. After priming has been finished collar 424 disengages from lead screw 41b. By now axially displacing button 5d, button 5d acts upon the lead screw to set up and dispense an amount of dose.

In a further different embodiment, shown in FIG. 15, the drive assembly is arranged within body 10. Body 10 has a channel 10a, which is slightly sloped or helical towards the distal end. Alternatively, instead of channel 10a, a recess on the inner sidewall of body 10 also forming a guiding track can be used. A projection arranged on the drive assembly 4, for instance on the lead screw nut or on the fixed pivot, engages channel or recess 10a. By rotating button 5, the whole drive assembly within body 10 is rotated along the guiding track or channel 10a. Due to the sloped or helical structure of the guiding track or channel, facing slightly towards the distal end, the drive mechanism advances and the gap between the most forward part of the drive assembly and a bung within a cartridge is closed. Any tolerances between the mechanical parts and particularly between the bung and the drive assembly are compensated. Further, the rotation may also expel a small amount of priming fluid or initiate a mixing step of two different substances within the cartridge.

In yet another embodiment, illustrated in FIG. 16A, button 5 and drive sleeve 42b are permanently and rigidly fixed together at the proximal end 420b of drive sleeve 42b. Lead screw 41b engages a thread on an internal surface of drive sleeve 42b as illustrated in FIG. 16A.

Drive sleeve 42b also comprises a projection 425b, for instance a lug which engages at a channel interface arranged in lead screw nut 46b. Again, the channel interface comprises a first portion and a second portion wherein the first portion is substantially perpendicular to the longitudinal direction of the drug delivery device while the second portion is substantially parallel to the longitudinal axis. By rotating button 5, the whole drive sleeve attached to button 5 is rotated as indicated in the figure. Projection 425b moves from the upper end to the lower end of the first portion during the rotation of the drive sleeve. As projection 425b reaches the lower end, projections 426b on the drive sleeve 42b snap into holding element 462b on the lead screw nut. This prevents a rotation in the reverse direction. From that point on, button 5b can be moved only into axial direction. Accordingly, the drive assembly of the drug delivery device is now in the ready state. The rotation of the drive sleeve (during preparation) causes the lead screw to advance in the distal direction by means of thread connections between the lead screw and drive sleeve and also the lead screw and lead screw nut.

A slightly different embodiment is illustrated in FIG. 16B, in which the channel within the lead screw nut comprises a further third portion arranged between the first and second portion and slightly sloped with respect to the first portion. As button 5 is rotated, projection 425b moves along the first portion and the second portion forcing drive sleeve 42b to slightly advance towards the distal end.

In addition, button 5 comprises a small projection 555 which engages a respective recess in body 10 after rotation of button 5 has been finished. The engagement between projection 555 and the respective recess in body 10 may prevent a small and undesired rotation of the drive sleeve.

FIG. 16C illustrates this embodiment in greater detail. Button 5 and drive sleeve 42b are permanently attached together at the proximal end 420b of drive sleeve 42b. Lead screw 41b engages a thread on an internal surface of drive sleeve 42b as illustrated. Projection 425b engages on the one hand lead screw 41 and on the other a respective channel interface in lead screw nut 46 or even in body 10. Projection 425b can act as an indicator if its position is visible to a user. For instance body 10 can be transparent in such area. By rotating button 5, drive sleeve 42b acts upon lead screw 41b driving the lead screw towards the distal end of the device. At the same time projection 425b slides along the cannel interface and thereby rejects the movement of the button to a pure rotation and later on to a pure axial movement.

The several aspects and features of the different embodiments shown herein can be combined in further ways without changing the scope of the proposed principle. In any case, the drive assembly prevents the user from an undesired set and dispense operation before the preparation of the drug delivery device has been finished by using two different button movements. For that purpose, the button, a collar or a similar object acts on the drive assembly in a pre-ready and transient state to prepare the drive assembly for the subsequent set and dispense operation. The movement of the button during the pre-ready state of the drive assembly is different from a subsequent movement of the button during the set and dispense operation.

Particularly, the movement of the button during the transient state of the drug assembly may comprise a pure rotational movement, a helical movement or a small axial movement combined with a rotational movement as well as a combination thereof. On the other hand, a movement of the button during the ready state of the drug delivery device may comprise an axial movement only. By these two different movements, which can also be indicated by externally visible markings, a user is able to distinguish whether the assembly of the drug delivery device is in the pre-ready state or in the ready state.

REFERENCE NUMERALS 1 assembly
4 drive assembly
5 button, button member
5b button
5d button
9 cartridge assembly, fluid reservoir
8 bung
7 cartridge holder
10 body
10a channel, guiding recess track
11 distal end, distal direction
12 proximal end, proximal direction
32, 34 parts of a pattern
41 piston rod
41a, 41b lead screw
41c lead screw
42 moving pivot
42a, 42b drive sleeve
43 non-return ratchet
44 lever
46 fixed pivot
46a lead screw nut
46b lead screw nut
47 carrier plate
49 drive sleeve
51 channel
52 helical guiding track, channel
53 clip, non-return ratchet
54 detent
55 helical guiding track
100 window
101 window
420b proximal end
421, 494 recess
422, 493 projection
423, 492 slanted surfaces
424a helically arranged projection
425b projection
426b projection
428, 429 end border elements
460 projection
461 lug, projection 462 holding element
462b holding element
490 markers, arrows
495 helically shaped surface
500 body finisher
501 button finisher
503 helically shaped projection
508 splines
505 collar
506 projection, lug
507 marker
511 first portion of channel
512 second portion of channel
550 thread
551 helically shaped surface
555 projection

The invention claimed is:

1. An assembly of a drug delivery device, comprising:
a body having a distal end and a proximal end;
a drive assembly arranged substantially within the body to facilitate dispense of a medicinal product, wherein facilitating dispense of the medicinal product comprises setting up a dose of the medicinal product and dispensing the dose;
a button member arranged at the proximal end of the body and adapted to act upon the drive assembly;
said drive assembly having an initial pre-ready state, a transient state and a ready state;
wherein in the pre-ready and transient state the button member is twistable with respect to the body to act upon the drive assembly as to prepare the drive assembly for subsequent use in the ready state, wherein in the initial pre-ready state and the transient state the drug delivery device is unable to set up the dose and unable to dispense the dose,
and wherein in the ready state the button member is axially moveable but not substantially twistable with respect to the body to act upon the drive assembly to set up and dispense the dose, wherein the drive assembly comprises a drive sleeve, operatively coupled to the button member, and a moving pivot, wherein the drive sleeve and the moving pivot each have a ramped interface that comprises a projection, a recess and a slanted surface, wherein (i) in the pre-ready state the drive sleeve is arranged disconnected from the moving pivot such that the projection of the drive sleeve is arranged opposite the slanted surface of the moving pivot and the projection of the moving pivot is arranged opposite the slanted surface of the drive sleeve, (ii) in the transient state the projection of the drive sleeve is guided along the slanted surface of the moving pivot and into the recess of the moving pivot and the projection of the moving pivot is guided along the slanted surface of the drive sleeve and into the recess of the drive sleeve and (iii) in the ready state the projection of the drive sleeve is disposed in the recess of the moving pivot and the projection of the moving pivot is disposed in the recess of the drive sleeve.

2. The assembly according to claim 1, wherein the drive assembly comprises at least one of:
a piston rod arranged within the body and axially displaceable towards the distal end of the body, wherein the drive sleeve is adapted to act upon the piston rod to axially displace the piston rod;
a fluid reservoir arranged at the distal end of the body, the fluid reservoir containing the medicinal product;
a bung to act upon the fluid reservoir to dispense the medicinal product.

3. The assembly according to claim 2, wherein the button member is adapted to act by a pure axial movement subsequent to a twist movement upon the drive member to set and dispense a dose of the medicinal product.

4. The assembly according to claim 2, wherein
the moving pivot is restricted to an axial movement within the body for driving the piston rod; and
the drive sleeve is arranged between the button member and the piston rod, wherein the piston rod and the drive sleeve comprise helically shaped surfaces that engage each other.

5. The assembly according to claim 2, wherein the button member is adapted to act by a twist movement upon the drive assembly during the transient state to prepare at least the drive sleeve and the moving pivot for dispensing the dose of the medicinal product.

6. The assembly according to claim 5, wherein the button member acts upon the drive assembly during the transient state to prime the drive assembly.

7. The assembly according to claim 5, wherein the button member acts upon the drive assembly during the transient state to mix a medicinal product with a fluid.

8. The assembly according to claim 1, wherein a twist movement of the button member in the pre-ready and in the transient state comprises a rotational or a helical movement.

9. The assembly according to claim 1, wherein the button member is purely rotatable in the pre-ready state or during the transient state.

10. The assembly according to claim 1, wherein the button member acts upon the drive assembly during the transient state to expel a priming portion of the medicinal product.

11. The assembly according to claim 1, wherein the drive assembly further comprises a retaining element adapted in the ready state to prevent the button member from being twisted with respect to the body.

12. The assembly according to claim 1, wherein the button member comprises a retaining element, the retaining element being adapted in the ready state to prevent the button member from being twisted with respect to the body.

13. The assembly according to claim 12, wherein the retaining element comprises a non-return ratchet having mating surfaces on the drive sleeve and the moving pivot.

14. The assembly according to claim 1, wherein the button member comprises a detent to releasably retain the button member in the pre-ready state to prevent undesired preparation.

15. The assembly according to claim 1, wherein the button member comprises a portion arranged on an outside of the body and coupled to the drive assembly, the portion adapted to be irreversible detached from the assembly during the transient state.

16. The assembly according to claim 1, wherein the movement of the button member during the transient state comprises at least some pure rotation.

17. The assembly according to claim 1, wherein the button member is oval shaped and the body has an oval shaped surface, wherein in the pre-ready state the oval shape of the button member is misaligned with the oval shaped surface of the body, in the transient state misalignment between the button member and the oval decreases and in the ready state the oval shape of the button member is aligned with the oval shaped surface of the body.

* * * * *